United States Patent [19]

Legro

[11] Patent Number: 5,623,781
[45] Date of Patent: *Apr. 29, 1997

[54] PILLS OR PELLETS CONTAINING SEEDS AND INERT CARRIER MATERIAL AND METHOD FOR THEIR PREPARATION

[75] Inventor: Robert J. Legro, Enkhuizen, Netherlands

[73] Assignee: Incotec B.V., Netherland

[*] Notice: The term of this patent shall not extend beyond the expiration date of Pat. No. 5,389,115.

[21] Appl. No.: 387,472

[22] Filed: Feb. 13, 1995

Related U.S. Application Data

[63] Continuation-in-part of Ser. No. 977,775, Nov. 17, 1992, Pat. No. 5,389,115.

[30] Foreign Application Priority Data

Nov. 21, 1991 [NL] Netherlands ............... 9101959

[51] Int. Cl.$^6$ .................................................. A01G 1/00
[52] U.S. Cl. ........................................ 47/576; 47/DIG. 9
[58] Field of Search .......................... 424/489; 435/174, 435/176, 177, 180, 181; 47/57.6; 71/64.01, 64.02, 64.04, DIG. 1, 57.6, DIG. 9

[56] References Cited

U.S. PATENT DOCUMENTS

| | | | |
|---|---|---|---|
| 2,736,139 | 2/1956 | Wise | 57/58.01 |
| 4,121,525 | 10/1978 | Courtis | 47/1.103 |
| 5,068,105 | 11/1991 | Lewis | 47/57.604 |

FOREIGN PATENT DOCUMENTS

| | | |
|---|---|---|
| 0977178 | 11/1975 | Canada. |
| 0206848 | 12/1986 | European Pat. Off.. |
| 2038316 | 2/1972 | Germany. |
| 0917736 | 4/1982 | U.S.S.R.. |
| 91/01803 | 2/1991 | WIPO. |

*Primary Examiner*—Gollamudi S. Kishore
*Attorney, Agent, or Firm*—D. Peter Hochberg; Mark Kusner; Michael Jaffe

[57] ABSTRACT

Pills or pellets containing seeds and inert carrier material, characterized in that the inert carrier material forms the core of the pills or pellets, while the seeds are distributed in a multitude around the core, adhering to that core in an adhesive layer, and method for the preparation of pills or pellets containing seeds and inert carrier material, characterized in that onto cores formed from inert carrier material a fluid adhesive containing seeds is applied, if necessary diluted with other material, in a quantity corresponding with at least two seeds per present inert core, making up the adhesive layer, or that the seeds are first mixed with a powdery adhesive, if necessary diluted with other powdery material in a quantity so that per present core at least two seeds are available, after which the mixture of seeds and at least adhesive, and simultaneous addition of fluid to form the adhesive layer, is applied to the core, and finally, if desired, the layer is dried.

10 Claims, 1 Drawing Sheet

PILLS OR PELLETS CONTAINING SEEDS AND INERT CARRIER MATERIAL AND METHOD FOR THEIR PREPARATION

CROSS-REFERENCE TO RELATED APPLICATION

This application is a continuation-in-part of U.S. Ser. No. 07/977,775, filed Nov. 17, 1992 now U.S. Pat. No. 5,389,115.

FIELD OF THE INVENTION

The invention relates to pills or pellets containing seeds and inert carrier material, and to a method for their preparation.

BACKGROUND OF THE INVENTION

Pills or pellets having multiple seeds and an inert carrier, and the methods of their preparation are known, for instance, from the abstracts Seed Treatments, "Developments and Prospects", by A. A. Powell and S. Mathews, Outlook on Agriculture, vol. 17, No. 3, 1988 and Technical and Commercial Aspects of Seed Pelleting and Film Coating, by P. Halmer, Proceedings of a Symposium by the BCPC, 1988.

In the known methods for pill making or pelletizing, the common essence is a target object, the seed, of which each individual part is covered, forming a pill or pellet, containing as a core one seed only. For most seeds this is desirable but for some it is not. Many flower seed pills could advantageously contain several seeds, but these cannot be covered by the existing methods.

Also, the existing methods are only suitable for making pills from or pelletizing relatively large seeds, as the pelletizing process is based on gravity. Covering small seeds individually meets with difficulties. In general the limit is a main or cross dimension of 300 µm, with difficulties arising with seeds below 500 µm. Seeds or spores, with dimensions in the order of 10–100 µm, such as for instance spores of ferns, fungi such as mushrooms and so on, cannot successfully be pelletized individually. Moreover, there is a definite need for several units of seeds per seed unit.

Therefore, there is a great demand for pills and pellets containing seeds and inert carrier material, as well as a method for the preparation of these pills or pellets by which seeds of small dimensions can also be pelletized and whereby the resulting pills may contain several seeds or spores.

SUMMARY OF THE INVENTION

Accordingly, the invention provides pills or pellets containing seeds and inert carrier material, characterized in that the inert carrier material forms the core of the pills or pellets, while the seeds are distributed in multiples around the core, adhering in an adhesive layer to that core.

The invention also comprises a method for the preparation of pills or pellets containing seeds and inert carrier material, characterized in that a fluid adhesive containing seeds, if necessary diluted with other material, in a quantity corresponding with at least two seeds per inert core, is applied to cores formed from inert carrier material, or that the seeds are first mixed with a powdery adhesive, if necessary diluted with other powdery material in a quantity per present core wherein at least two seeds are included, after which the mixture of seeds and at least adhesive, to which fluid has been simultaneously added to form the adhesive layer, is applied to the core, and finally, if desired, the layer is dried.

It has been shown that such multi-seed pills, of which the core is formed from inert carrier material and the seeds are distributed in a multitude around the inert core in an adhesive layer, allow good and more or less reproducible sowing of small seeds or spores such as fern spores, spores of fungi of 10–100 µm, as well as fine seed of 60–1000 µm.

For the fluid adhesive one uses as a rule one of the usual adhesives known for pelletizing purposes, such as polymers which are dispersible or soluble in water, for instance polyvinyl alcohol, polyvinyl pyrrolidone, polyvinyl acetate, cellulose derivatives, as well as copolymers and related polymers.

As the solid powdery mixture one uses as a rule one of the usual fillers and binding materials known for pelletizing purposes, such as clay, cellulose powder, chalk, vermiculite, turf, perlite, talcum and quartz flour. If desired, fillers, pigments, etc. may be added to the formulation of the adhesive layer.

According to the invention one can use glass beads or perlite granules as an inert core material. The cores may be individually provided with an adhesive layer, wherein, for instance, the seeds or spores are applied in a desired concentration by means of a solid or fluid formulation.

According to the invention a material can be used for the inert core which, under the influence of fluid, swells and then disintegrates or collapses and dissolves, which causes optimal spreading of, for example, the seeds or spores in the cells of a seed tray.

If desired one can enclose in the adhesive layer or in the mixture of seeds and adhesive an insecticide and/or fungicide, for the protection of the seeds. Also, the physical and/or chemical properties of the adhesive layer can be determined such that optimal development, that is to say germination and growth of the target object, is achieved. This is called the microclimate. This can mean that the oxygen/water ratio can be adjusted as well as the pH, and that pesticides, bio-stimulators or specific nutrients can be added.

Characteristic for the invention is the presence per pill of at least 2 seeds, usually more than 5 seeds, increasing to several times ten (for example fern spores) or to hundreds to thousands (for example fungal spores, bacteria).

BRIEF DESCRIPTION OF THE DRAWINGS

The invention is elucidated with reference to the accompanying drawing, in which.

DETAILED DESCRIPTION OF THE PREFERRED EMBODIMENT

Figure 1:
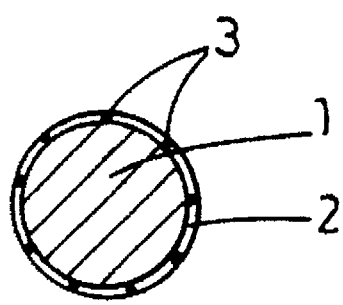
FIG. 1 is an enlarged cross-section of a pill according to the invention.

Referring now to the drawings wherein the showings are for the purpose of illustrating the preferred embodiment of the invention, and not for the purpose of limiting same.

The essence of the known coating system is that one departs from the seed as the core, whereby the core material or the stationary phase consists in principle of the target object which finally is to expand. In general these cores are seeds. Around the core a layer is applied which, since it has to form a shape, could be called the mobile phase. This mobile phase may be fluid, and this can be applied using a film coating process, which characteristically takes its course while simultaneously drying. The mobile phase can, however, also occur in powder form, whereby during simultaneous administration of fluid, a layered build-up takes place until a pill or pellet has reached the desired size. This mobile phase is in principle free of seeds and consists largely of inert carrier material, although active substances such as pesticides may be included.

In other words, the mobile phase is a matrix of solids and/or liquids which is shaped and formed around the stationary phase, i.e., the core. The mobile phase is the carrier for the target object (the seeds) and possibly other material. Unlike the core, the mobile phase is often not inert.

In the multi-seed concept the principle is exactly reversed. As the basis or stationary phase one departs from the inert core material and the target object, essentially several units, are placed around the core via the mobile phase. This can be done in different ways, in one or more layers.

FIG. 1 shows a pill in cross-section wherein the seeds 3 are applied in several units in a thin adhesive layer 2 around a core 1 of inert carrier material. This embodiment is very satisfactory if many more need not be added to the seeds and/or if the material is to be applied in particular to the outside.

Figure 2:
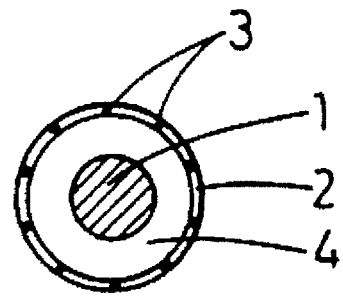
FIG. 2 is an enlarged cross-section of a second embodiment.

FIG. 2 shows another embodiment in cross-section, whereby first a somewhat thicker intermediate layer 4 is built up around a smaller core 1, which intermediate layer could be intended to include substances which may promote optimal development, germination, and growth, in other words for the microclimate. Around the intermediate layer 4, which here determines the final size of the pill, a thin adhesive layer 2 is applied with a multitude of seeds 3.

Figure 3:
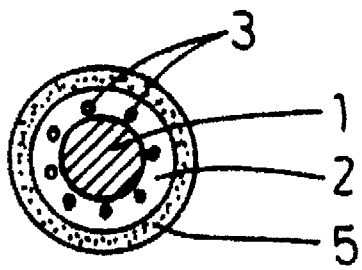
FIG. 3 is an enlarged cross-section of a variation on the second embodiment.

FIG. 3 shows another embodiment of the two-layer-type (FIG. 2), in which first a thicker adhesive layer 2 with filler is applied around the smaller core 1, with the multitude of seeds 3 distributed over it, and finally a coating 5 is applied over the whole. This coating may sometimes be necessary to give the pill a smooth finish.

Figure 4:
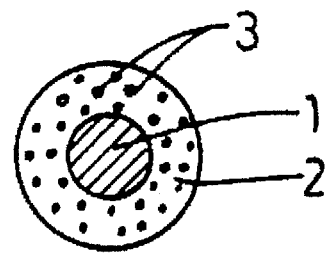
FIG. 4 is an enlarged cross-section of a variation on the embodiment in FIG. 1.

FIG. 4 shows a variation on the embodiment of FIG. 1. Here the core 1 is small, but the adhesive layer 2 is thick and suitable for inclusion of additives and of larger amounts of seeds 3.

In all these cases the term "core 1" means the totally inert basic material, that is to say the stationary phase. The intermediate layer 4, consisting also essentially of carrier material, also called mobile phase, is a layer that may optionally be applied underneath the final adhesive layer 2, which contains the target object (multitude of seeds 3).

The adhesive layer 2 is also part of mobile phase and may be applied as solid or fluid form, but contains several units of the target object. The adhesive layer 5 is the mobile phase, applied for the finish and contains no target object.

The core material may be organic or inorganic, and of natural or synthetic origin. Examples are glass beads (solid as well as hollow), little plastic balls, selected perlite granules, selected granulates (possibly on sugar basis or on another water soluble basis, so that the core is completely dissolved in the ground), bentonite granulates that will dissolve with moisture, flowing away in the ground from the pill or pellet, and the like.

Granulates on a water soluble basis refers to water soluble granules for using a core for multi-seed pills. The core dissolves when the multi-seed pill absorbs water, and the pill collapses yielding a tight distribution of the seeds. If the core remains after absorbing water, the seeds remain on the top of the core rather than on the desired location on top of the soil.

The basis of the adhesive layer, the optional intermediate layer and the optional coating layer will consist of the same substances that are used in conventional pelletizing and film coating. Examples of substances in the optional intermediate layer and in the adhesive layer are:

in the powdery basis:
    clay, cellulose powder, chalk, vermiculite, turf, perlite, talcum, quartz flour, and in the fluid basis:
    water-dispersible or -soluble polymers such as polyvinyl alcohol, polyvinyl pyrrolidone, cellulose derivatives, copolymers and related polymers, these extend to the outside layer, which in many cases is the adhesive layer, and pigments may be added if desired. The adhesive layer or binding substance can thus be organic (polyvinyl acetate, polyvinyl alcohol, polyvinyl pyrrolidone, cellulose derivatives), or inorganic (bentonite, clay, gypsum).

There is no lower limit for the multi-seed concept, but in practice the smallest workable dimension for, for example spores of different origin, will be around 10–60 µm. A defined upper limit is also difficult to indicate. The larger the target object becomes, the more difficult it will be for the concept to be carried out. The lower limit for conventional pelletizing (based on gravity) lies around 300 µm. The multi-seed concept is in any case still applicable for objects of up to about 1000 µm. Tests with lobelia seed of an average size of 575 µm and a thickness of 350 µm were reasonably successful (75% in the desired distribution).

The invention is particularly directed to seeds having a cross dimension (the dimension through the thickest part of the object, i.e., the seed; for spherical objects, this would be the diameter) of from 100 µm to 1000 µm. These seeds can be broken down into flower seeds (e.g., begonia, lobelia, alyssum, etc.), herb seeds (e.g., parsley), wild flower seeds (e.g., papaver) and other fine seeds (e.g., tobacco, orchid).

The size of the core may vary between 0.5 and 3 mm in diameter, but these sizes must not be considered to be absolute. The size of the end-product may also vary a lot, depending on the intended purpose. Usually the final size will be between 1 mm round and 4 mm slot, which is the same as the usual seed pills. (The indications "round" and "slot" refer to the type of screen with which the size is measured. "Slot" refers to holes in screens which are enlogated or oval shaped. Slot screens used for pills which are not round, but oval, are shaped accordingly.) The appearance of the pills is no different form the pills available according to the prior art so that they can also be sown using the existing sowing devices. This is very important for the preferred embodiments of the invention, since growers of plants using the pellets according to the invention need not have to buy different kinds of sowing machinery and/or sowing plates or belts. It is very advantageous using existing seed-sowing machines.

The core for multi-seed use is in a stationary phase. It is both biologically and chemically inert to the target material. The core can have a regular shape or an irregular shape. Its size is between 0.5 mm and 3.0 mm. The cores for multi-seed use, having seeds from 100 µm to 1000 µm, have a cross dimension of from 0.5 mm to 3.0 mm.

The pellet, incorporating the core, the intermediate layer consisting essentially of the carrier material, the multi-seed portion and the adhesive layer, generally has a cross dimension of from 1 mm to 4 mm.

The invention is further elucidated with the aid of the following non-limitative examples.

EXAMPLE I

Multi-seed fern spores

The size of the fern spores under consideration is about 50 μm. A dispersion is prepared of the fern spores in a watery solution of 3% polyvinyl alcohol, adjusting the concentration of the spores in the dispersion to the desired number per pill, in this particular case 20 spores per pill. The dispersion is acidified to the assumed optimal pH of 5.5–6.0.

In a fluid bed film coater, laboratory model, 50,000 plastic granules (because of low density these are easier to fluidize than, for instance, glass beads) being 2.5–3.0 mm round, are coated with the prepared dispersion of 20 spores per pill in the manner that is usual for seeds and dried simultaneously, whereby an adhesive layer is formed on the granules containing the spores in random distribution.

EXAMPLE II

Multi-seed fern spores

The size of the fern spores is about 50 μm. From these spores a dry mixture is prepared with inert powder material consisting mainly of clay and quartz flour, whereby the concentration of the spores in the powder material is adjusted to the desired number per pill, in this particular example this is 20 spores per pill. The mixture is acidified to the assumed optimal pH of 5.5–6.0 (measured after dilution with water).

100,000 glass granules being 0.75 mm round—1.00 mm slot, are placed in a coating drum with a diameter of 55 cm. As it is not desirable to end up with too large a glass granule, a relatively small glass granule and a two-phase coating was chosen, applying first, as intermediate layer, a carrier material around the relatively small core. This material will eventually dissolve into the ground. The carrier material used in this example again consists mainly of clay and quartz flour. The intermediate layer is applied until the dimension reaches from 1.75–2.00 mm slot.

Lastly, the final adhesive layer with the spores is applied onto the intermediate layer, realizing a final dimension of 2.25–2.50 mm slot. Both the intermediate layer and the adhesive layer are applied while simultaneously a liquid spray on a water basis containing 5% polyvinyl alcohol is applied. Finally the multi-seed pills are dried by the method that is usual for drying seed pills. The coating process is not essentially different from the conventional coating process.

EXAMPLE III

Multi-seed lobelia seeds

Lobelia seeds are about 600 μm long and about 300 μm thick. The seeds are mixed in the desired concentration with an inert powder material mixture consisting mainly of clay, quartz flour and coarse fiber whereby the differently sized granules are distributed so as to keep separation of the relatively large seeds during the process to a minimum. The concentration of the seeds in the mixture is adjusted to 5–10 seeds per pill.

100,000 selected perlite granules having a diameter of 1.50–1.75 mm slot, are placed in a coating drum with a diameter of 55 cm. The rough surface of the perlite granules forms a good basis for adhesion for the coarse mixture. With the aid of a watery solution of 5% carboxymethyl cellulose, a thick adhesive layer is applied while alternating moistening with sprinkling the powdery mixture (in the same way as with the conventional coating system).

The pill is further smoothly finished with the aid of an inert powder mixture consisting mainly of clay, quartz flour and talcum, realizing a final size of 3.0–3.5 mm slot. Finally the multi-seed pills are dried by the method that is usual for drying seed pills.

EXAMPLE IV

Multi-seed fungal spores

The size of the fungal spores is about 15–35 μm. The spores are mixed in the desired concentration with a inert powder material mixture consisting mainly of clay, wood flour and quartz flour. The concentration of the fungal spores in the of clay, wood flour and quartz flour. The concentration of the fungal spores in the mixture is adjusted to about 3000 spores per pill.

100,000 glass granules having a diameter of 0.75 mm round—1.00 mm slot, are placed in a coating drum with a diameter of 55 cm. A thick adhesive layer is then applied around the glass granules by alternating moistening with a liquid spray consisting of a 10% polyvinyl acetate in water and sprinkling on the mixture, realizing a final size of 3.0–3.5 mm slot. Dependent on utilization, the multi-seed pills may be left moist (limited storage time at a low temperature) or be partly or totally dried for ultimate use.

EXAMPLE V

Multi-seed alyssum seeds

Alyssum seeds with an average length of 825 μm and an average width of 675 μm are mixed in a desired concentration with an inert powder mixture consisting mainly of clay and vermiculite granules in a particle distribution ranging from about 15 μm to 750 μm in size. The number of seeds is targeted at an average of five seeds per pill.

250,000 accurately selected, irregular-shaped ground cork particles which are screened at an average diameter of 2.0 mm are placed in a slowly rotating coated drum with a diameter of 80 cm. The cavities of the irregular shaped cork particles are a good base for the relatively large alyssum seeds to be fixed to. The cork particles are wetted with a watery solution of a polyethylene glycol 3400 solution with a density of 1.050. The PEG-solution has good sticking properties for the seeds to adhere to the cork particles.

The mixture of alyssum seeds with clay and vermiculite is applied onto the cork particles while alternating the sprinkling of the seed mixture with spraying of the PEG-solution. The pill is further smoothly finished with an inert powder mixture consisting mainly of clay, quartz flour and talcum, realizing a final size of 3.5–4.0 mm slot. The multi-seed pills are finally dried by the method used for drying seed pills.

EXAMPLE VI

Multi-seed exacum seeds

The size of the exacum seed used in this example ranges from 110–140 μm. Since the seeds are very small, a multi-seed concept is chosen where the seeds will be located in an outer surface layer of the final multi-seed pill. In order to optimize the distribution of seeds in the pills, the seed is premixed in a desired concentration with pumice particles which have a particle distribution of 75–150 μm. The pumice particles have a density which compares well with the exacum seeds.

In this particular example the objective is an average of seven seeds per pill. 50,000 round shaped plastic beads with a diameter of 0.5 mm are placed in a rotating drum of 35 cm and sprayed with a 10% watery solution of a maltodextrine until beads tend to stick together. An amount of the seed and pumice mixture is then added until the beads are rolling freely again. This process is repeated until the seed pumice mixture is completely absorbed in a thin surface layer on the beads. During the application of seed mixture and binding solution, the excess moisture is evaporated by blowing hot air from a small hot air blower into the pan. After the seed mixture is applied, the spraying of binder solution and drying is continued for a short period of time in order to further fix the seed mixture in the surface layer of the multi-seed pills.

EXAMPLE VII

Multi-seed begonia seeds

The oval shaped begonia seeds used in this example have an average length of 310 μm and an average width of 165 μm. The seeds are mixed with an inert powder mix of clay, wood flour and pumice particles which has a particle distribution of 2–210 μm. The concentration of seeds in the mixture is adjusted to an average of ten seeds per pill. 100,000 round glass beads, carefully screened to a diameter of 0.80–1.0 mm round, are put in a rotating coating drum with a diameter of 55 cm. The glass beads are coated with a basic inert mixture of clay, wood flour and pumice particles while spraying a watery solution of 3% polyvinyl alcohol until a size of 1.5–1.6 mm is realized. These basic pills are subsequently coated with the seed mixture while spraying with the PVOH-solution. During the application of the seed mixture, a screening and enlargement phase is applied to narrow down the final size distribution of the pills and thus to narrow down the distribution of the number of seeds per pill. Finally, the pills are smoothly finished with a fine powder mixture of mainly clay, quartz flour and talcum, realizing a final size of 1.75–2.1 mm slot. The multi-seed pills are dried back according to the drying method that is usual for drying seed pills.

The invention has been described with particular emphasis on the preferred embodiments thereof, but variations and modifications may occur to those skilled in the art to which the invention pertains.

Having described the invention, the following is claimed:

1. A multi-seed pellet comprising:

a core comprising a substance biologically and chemically inert to seeds in said multi-seed pellet, said core selected from the group consisting of glass beads, perlite granules, plastic balls and bentonite granulates; and an adhesive layer surrounding the core and comprising at least two seeds, each of said seeds having a cross dimensional size of 10 μm to 1000 μm, said adhesive layer holding the seeds to the core and selected from the group consisting of polyvinyl alcohol, polyvinyl pyrrolidone, polyvinyl chloride, polyvinyl acetate, clay, bentonite, gypsum, cellulose powder, chalk, vermiculite, turf, perlite, talcum and quartz flour.

2. A multi-seed pellet according claim 1 wherein the seeds have a cross dimension of 100 μm to 1000 μm.

3. A multi-seed pellet according to claim 1 wherein said core has a cross dimension of 0.5 mm to 3.0 mm.

4. A multi-seed pellet according to claim 1 wherein said glass beads consist of hollow glass beads and solid glass beads.

5. A multi-seed pellet according to claim 1 wherein the seeds are domestic flower seeds, herb seeds, wild flower seeds, and vegetable seeds.

6. A multi-seed pellet comprising:

a core comprising a substance biologically and chemically inert to seeds in said multi-seed pellet, said core selected from the group consisting of glass beads, perlite granules, plastic balls and bentonite granulates;

an intermediate layer surrounding said core said intermediate layer being selected from the group consisting of clay, cellulose powder, chalk, vermiculite, turf, perlite, talcum, quartz flour, pumice, wood flour, polyvinyl alcohol and polyvinyl pyrrolidone; and an adhesive layer surrounding said intermediate layer, said adhesive layer being selected from the group consisting of polyvinyl alcohol, polyvinyl chloride, polyvinyl pyrrolidone, polyvinyl acetate, bentonite, clay, gypsum, cellulose powder, chalk, vermiculite, turf, talcum and quartz flour; and at least two seeds, each of said seeds having a cross dimensional size of 10 μm to 1000 μm, disposed in said adhesive layer.

7. A multi-seed pellet according to claim 6 wherein the seeds are selected from the group consisting of domestic flower seeds, herb seeds, wild flower seeds, and vegetable seeds.

8. A multi-seed pellet according to claim 6 wherein said intermediate comprises substances for the germination, development and growth of the seeds.

9. A multi-seed pellet according to claim 6 wherein the largest of the seeds has a cross dimension of 100 μm to 1000 μm.

10. A multi-seed pellet according to claim 6 wherein the core has a cross dimension of 0.5 mm to 3.0 mm.

* * * * *